(12) United States Patent
Ji et al.

(10) Patent No.: US 8,003,089 B2
(45) Date of Patent: Aug. 23, 2011

(54) Y SHAPE BRANCHED HYDROPHILIC POLYMER DERIVATIVES, THEIR PREPARATION METHODS, CONJUGATES OF THE DERIVATIVES AND DRUG MOLECULES, AND PHARMACEUTICAL COMPOSITIONS COMPRISING THE CONJUGATES

(75) Inventors: Shishan Ji, Beijing (CN); Dequan Zhu, Beijing (CN)

(73) Assignee: Beijing Jiankai Technology Co., Ltd., Beijing (CN)

( * ) Notice: Subject to any disclaimer, the term of this patent is extended or adjusted under 35 U.S.C. 154(b) by 1701 days.

(21) Appl. No.: 10/507,452

(22) PCT Filed: Mar. 12, 2003

(86) PCT No.: PCT/CN03/00179
§ 371 (c)(1),
(2), (4) Date: Apr. 12, 2005

(87) PCT Pub. No.: WO03/076490
PCT Pub. Date: Sep. 18, 2003

(65) Prior Publication Data
US 2005/0180946 A1    Aug. 18, 2005

(30) Foreign Application Priority Data
Mar. 13, 2002    (WO) .................. PCT/CN02/00147

(51) Int. Cl.
*A61K 31/77*        (2006.01)
*A61K 47/48*        (2006.01)
(52) U.S. Cl. .................... 424/78.38; 525/54.1; 525/54.2
(58) Field of Classification Search .................. None
See application file for complete search history.

(56) References Cited

U.S. PATENT DOCUMENTS

| | | | |
|---|---|---|---|
| 3,855,156 A * | 12/1974 | Marumo ....................... | 510/480 |
| 5,122,614 A | 6/1992 | Zalipsky et al. | |
| 5,349,001 A | 9/1994 | Greenwald et al. | |
| 5,382,657 A * | 1/1995 | Karasiewicz et al. ......... | 530/351 |
| 5,643,575 A | 7/1997 | Martinez et al. | |
| 5,672,662 A * | 9/1997 | Harris et al. ................... | 525/408 |
| 5,824,701 A * | 10/1998 | Greenwald et al. ........... | 514/449 |
| 5,840,900 A | 11/1998 | Greenwald et al. | |
| 5,879,923 A | 3/1999 | Yago et al. | |
| 5,977,163 A | 11/1999 | Li et al. | |
| 6,153,655 A | 11/2000 | Martinez et al. | |
| 6,262,107 B1 | 7/2001 | Li et al. | |
| 7,498,035 B2 | 3/2009 | Ji et al. | |
| 2002/0009426 A1 | 1/2002 | Greenwald et al. | |
| 2005/0147617 A1 | 7/2005 | Ji et al. | |
| 2010/0221213 A1 | 9/2010 | Ji et al. | |

FOREIGN PATENT DOCUMENTS

| | | |
|---|---|---|
| CN | 1 164 533 | 11/1997 |
| CN | 1 283 643 | 2/2001 |
| DE | 3 730 797 | 3/1989 |
| EP | 411461 | 2/1991 |
| EP | 505163 | 7/1996 |
| EP | 1580216 | 9/2005 |
| GB | 1313313 | 4/1973 |
| GB | 2215806 | 3/1984 |
| WO | WO 97/01631 | 1/1997 |
| WO | WO01/57067 | 8/2001 |
| WO | WO03/074586 | 9/2003 |
| WO | WO03/076490 | 9/2003 |
| WO | WO03/101476 | 12/2003 |

OTHER PUBLICATIONS

Greenwald et al., "Highly Water Soluble Taxol Derivatives: 7-Polyethylene Glycol Carbamates and Carbonates", *Journal Organic Chemistry*, 60: 331-336, 1995.
Greenwald et al., "Drug Delivery Systems: Water Soluble Taxol 2'-Poly(ethylene glycol) Ester Prodrugs-Design and in Vivo Effectiveness", *Journal of Medical Chemistry*, 39: 424-431, 1996.
Communication pursuant to Article 96(2) EPC corresponding to European Application No. 03 711 787.6-1216 dated May 12, 2006.
Communication pursuant to Article 157(2)(a) EPC corresponding to European Application No. 03 711 787.6-2115 dated Oct. 8, 2006.
English Language Abstract of JP60096605A2: Production of Hydrophilic Resin to Misubishi (May 30, 1985).
Notice of Allowance corresponding to U.S. Appl. No. 10/506,524 dated Oct. 20, 2008.
Official Action corresponding to U.S. Appl. No. 10/506,524 dated Dec. 1, 2006.
Official Action corresponding to U.S. Appl. No. 10/506,524 dated May 31, 2007.
Official Action corresponding to U.S. Appl. No. 10/506,524 dated Aug. 6, 2007.
Official Action corresponding to U.S. Appl. No. 10/506,524 dated Mar. 25, 2008.
Official Action corresponding to U.S. Appl. No. 10/506,524 dated Sep. 10, 2008.
[Retrieved from]http://web.archive.org/web/20000414203748/http://members.aol.com/logan20/outline1.html 2000, 4 pages, [Retrieved on Jul. 6, 2007].
Solomons, et al., *Organic Chemistry*, 2004. John Wiley & Sons., 3 pages.
Bailey, F.E., *Alkylene Oxides and Their Polymers*, 1-5, New York, 1991. Harris, J. Milton, *Polyethylene Glycol Chemistry Biotechnical and Biomedical Applications*, 1-12, Plenum Press: New York, 1992.
Seligson et al., "A New Prodrug of Paclitaxel: Synthesis of Protaxel", *Anti-Cancer Drugs*, 12: 305-313, 2001.
International Search Report corresponding to International Application No. PCT/CN03/00164 dated Jun. 12, 2003.
International Preliminary Examination Report for PCT/CN03/00179 dated Nov. 17, 2003.
International Search Report for PCT/CN03/00179 dated Jun. 16, 2003.
Official Action corresponding to U.S. Appl. No. 12/781,173 dated Jan. 26, 2011.

* cited by examiner

*Primary Examiner* — Tracy Vivlemore
*Assistant Examiner* — Thurman Wheeler
(74) *Attorney, Agent, or Firm* — Jenkins, Wilson, Taylor & Hunt, P.A.

(57) ABSTRACT

The present invention relates to Y-shape branched PEG derivatives of formulae (I) to (IV). The present invention also relates to conjugates of these Y-shape derivatives and drug molecules, pharmaceutical compositions comprising those conjugates.

29 Claims, 7 Drawing Sheets

Y SHAPE BRANCHED HYDROPHILIC POLYMER DERIVATIVES, THEIR PREPARATION METHODS, CONJUGATES OF THE DERIVATIVES AND DRUG MOLECULES, AND PHARMACEUTICAL COMPOSITIONS COMPRISING THE CONJUGATES

FIELDS OF THE INVENTION

The present invention relates to Y-shape branched hydrophilic polymer derivatives, their preparation methods, and conjugates of the derivatives and drug molecules, especially proteins and polypeptides. This invention also relates to pharmaceutical compositions comprising the conjugates.

BACKGROUND OF THE INVENTION

Natural and recombinant proteins and polypeptides have been used as medicines. The products after purification and separation can be used to treat specific diseases by parenteral routes. When administered parenterally, however, proteins may have immunogenecity, or be relatively insoluble in water, or have short pharmacological half-lives. How to raise and keep a highly effective serum concentration in vivo is of significant importance.

In addition to proteins, clinically there is necessity to modify other constituents of natural medicine such as flavonoids, terpenoids, anthraquinones, steroids and alkaloids to prolong their physiological half-lives, enhance their stability and the possibility to reach the target site, raise their solubility in water, change administration routes and improve bioavailability.

Recently PEG has been widely used to conjugate proteins, peptides or other therapeutic agents, in order to prolong their physiological half-lives and lower their immunogenicity and toxicity. Clinically, PEG and its derivatives have been widely used as carriers in the manufacture of pharmaceutical preparations of commercial drugs. The methods for conjugating PEG to drug molecules has made much progress in the last 10 years and had been applied to many officially approved drugs. For example, PEG-intron®, a conjugate of PEG to α-interferon, exhibits longer circulation half-life and better therapeutic effect. The conjugate of PEG to paclitaxel reduces the toxicity and increases the bioactivity. The metabolism of PEG is well known, and PEG is accepted as a safe drug modifier.

One process called PEGylation is often applied when conjugating PEG to drugs. Namely, one or two of the terminal groups of the PEG are activated to form a proper functional group, which is reactive to at least one functional group of the drugs, and can form a stable bond with it.

Many PEG derivatives have been reported. Linear PEG propionic acid, butanoic acid and their NHS esters have been reported in U.S. Pat. No. 5,672,662. Recently a U-shape branched PEG is reported in U.S. Pat. No. 564,357. In these PEG derivatives, two linear PEGs link to one molecule or structure through two identical functional groups, such as two amino groups or two carboxyl groups. In one example of the patent, the branched PEG is derived from linear PEG and lysine, which is a kind of amino acid having two amino groups.

SUMMARY OF THE INVENTION

The present invention provides a new Y-shape branched hydrophilic polymer derivative, which is represented by formula I:

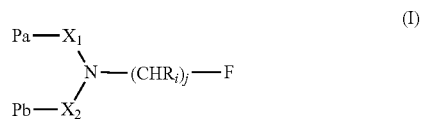

(I)

wherein $P_a$ and $P_b$ are hydrophilic polymers, which are the same or different;

j is an integer from 1 to 12;

$R_i$ is selected from the group consisting of H, a $C_{1-12}$ substituted or unsubstituted alkyl, a substituted aryl, an aralkyl, and a heteroalkyl;

$X_1$ and $X_2$ independently are linking groups, wherein $X^1$ is $(CH_2)_n$, and $X_2$ is selected from the group consisting of $(CH_2)_n$, $(CH_2)_nOCO$, $(CH_2)_nNHCO$ and $(CH_2)_nCO$, wherein n is an integer of from 1-10; and F is a functional group selected from the group consisting of a hydroxyl group, a carboxyl group, an ester group, carboxylic acid chloride, hydrazide, maleimide and pyridine disulfide, being capable of reacting with an amino group, a hydroxyl group or a thiol group of a therapeutic agent or a substrate to form a covalent linkage.

According to another aspect of the invention, there is provided a Y-shaped branched poly(ethylene glycol) derivatives represented by formula II:

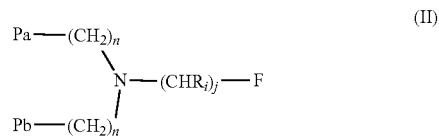

(II)

wherein $P_a$ and $P_b$ are polyethylene glycols, which are the same or different;

n and j are independently an integer from 1 to 12;

$R_i$ is selected from the group consisting of H, a $C_{1-12}$ substituted or unsubstituted alkyl, a substituted aryl, an aralkyl, and a heteroalkyl; and F is a functional group selected from the group consisting of a hydroxyl group, a carboxyl group, an ester group, carboxylic acid chloride, hydrazide, maleimide and pyridine disulfide, being capable of reacting with an amino group, a hydroxyl group or a thiol group of a therapeutic agent or a substrate to form a covalent linkage.

According to still another aspect of the invention, there is provided a Y-shaped branched poly(ethylene glycol) derivatives represented by formula III:

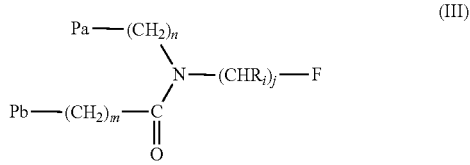

wherein
$P_a$ and $P_b$ are polyethylene glycols, which are the same or different;
n, m and j are independently an integer from 1 to 12;
$R_1$ is selected from the group consisting of H, a $C_{1-12}$ substituted or unsubstituted alkyl, a substituted aryl, an aralkyl, and a heteroalkyl; and
F is a functional group selected from the group consisting of a hydroxyl group, a carboxyl group, an ester group, carboxylic acid chloride, hydrazide, maleimide and pyridine disulfide, being capable of reacting with an amino group, a hydroxyl group or a thiol group of a therapeutic agent or a substrate to form a covalent linkage.

According to still another aspect of the invention, there is provided a Y-shaped branched poly(ethylene glycol) derivatives represented by formula IV:

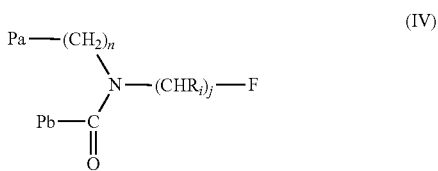

wherein
$P_a$ and $P_b$ are polyethylene glycols, which are the same or different;
n and j are independently an integer from 1 to 12;
$R_i$ is selected from the group consisting of H, a $C_{1-12}$ substituted or unsubstituted alkyl, a substituted aryl, an aralkyl, and a heteroalkyl; and
F is a functional group selected from the group consisting of a hydroxyl group, a carboxyl group, an ester group, carboxylic acid chloride, hydrazide, maleimide and pyridine disulfide, being capable of reacting with an amino group, a hydroxyl group or a thiol group of a therapeutic agent or a substrate to form a covalent linkage.

According to still another aspect of the invention, there is provided a method to prepare the PEG derivative of formula II, comprising:
  at 0° C. initiating the polymerization of ethylene oxide with N,N-di-2-hydroxylethyl-2-benzyloxyethyl amine in the presence of a catalyst;
  alkylating terminal hydroxyl groups;
  removing benzyl groups by catalytic hydrogenation; and
  derivatizing the new hydroxyl group to incorporate the terminal group F.

According to still another aspect of the invention, there is provided a method to prepare the PEG derivatives of formulae (II) and (III), comprising:
  reacting one methoxyl polyethylene glycol mesylate with an amino acid under basic conditions,
  reacting the product obtained above with another methoxyl polyethylene glycol derivative, and further derivatizing to incorporate a terminal group F.

According to still another aspect of the invention, there is provided conjugates of the above polymer derivatives and drug molecules through the functional group F.

According to still another aspect of the invention, there is provided pharmaceutical compositions comprising the above conjugates.

DETAILED DESCRIPTION OF THE INVENTION

Figure 1:
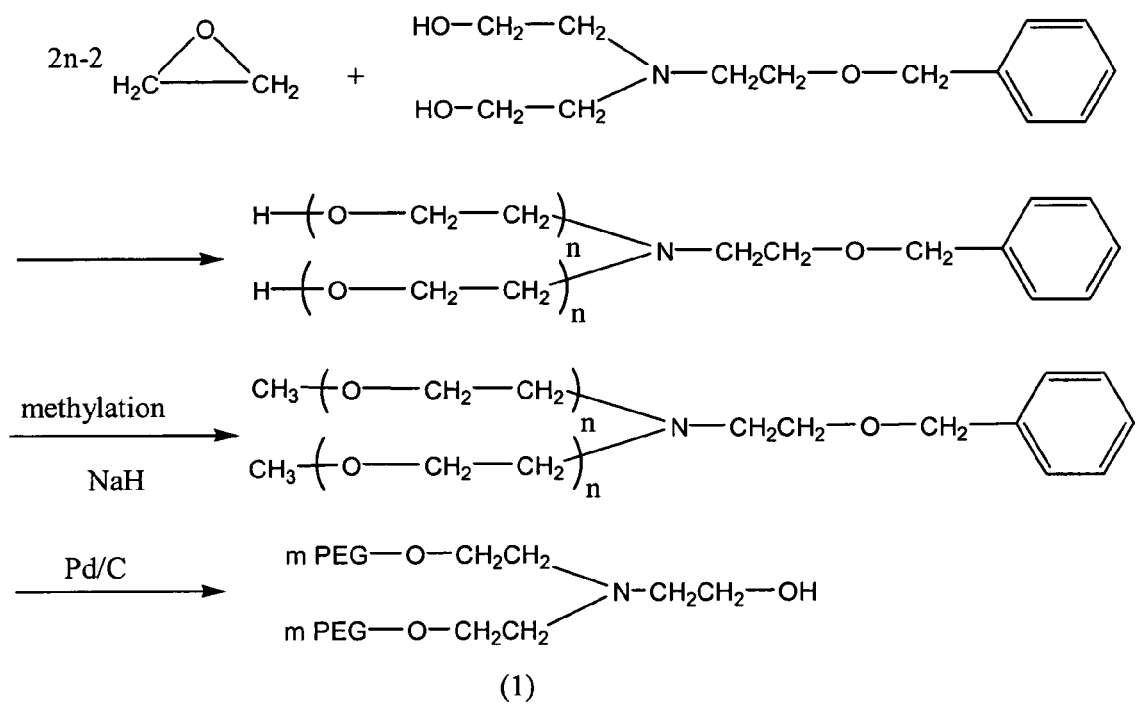
FIG. 1 shows the synthesis of Y-shape branched polyethylene glycol derivatives (1).

In the present invention, the hydrophilic polymer is, for example, a polyethylene glycol, a polypropylene glycol, a polyvinyl alcohol, a polyacrylmorpholine or a copolymer thereof, especially preferred are a polyethylene glycol and copolymers thereof.

In the PEG derivatives of formulae (II) to (IV) of the present invention, Pa and Pb may be the same or different, and can be the PEG represented by the following formula (V):

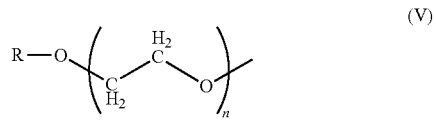

wherein:
R is H, a $C_{1-12}$ alkyl, cycloalkyl or aralkyl; and
n is an integer, representing the degree of polymerization, preferably making the molecular weight of PEG is 300 to 60000.

In formula (V), R is preferably H, methyl, ethyl, isopropyl, cyclopropyl, cyclobutyl, cyclohexyl or benzyl.

The Y-shaped branched hydrophilic polymer derivatives of the present invention are preferably prepared by attaching two linear PEG chains to an amino group of a small molecule.

PEG is used here as an example to illustrate the preparation of Y-shaped branched hydrophilic polymer derivatives of the present invention.

The general structure of PEG is as the formula below:

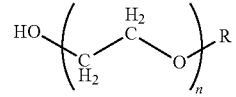

wherein:

R is H, a $C_{1-12}$ alkyl, a cycloalkyl base or an aralkyl, and n is an integer, representing the degree of the polymerization.

As a lower alkyl, R can be any lower alkyl group having 1-6 carbon atoms, for example, methyl, ethyl, n-propyl, iso-propyl, n-butyl, iso-butyl, n-pentyl, or n-hexyl. As a cycloalkyl, R is preferably a cycloalkyl containing 3-7 carbon atoms, for example, cyclopropyl, cyclobutyl, and cyclohexyl. Among those, cyclohexyl is more preferable. The typical compound is methoxy-polyethylene glycol (mPEG). Other analogs and derivatives of polyethylene glycol, such as polypropylene glycols, polyvinyl alcohols, and polyacrylmorpholines and the like, can also be used in the present invention.

In respect of PEGs, they are usually measured by molecular weight. It is preferred that the molecular weight of PEG which forms the conjugates falls in the range from 300 to 60000 Daltons, which means n is about 6 to 1300. It is more preferred that n is 28, 112 and 450, respectively corresponding to molecular weight of 1325, 5000, and 20000. Because of the potential non-homogeneity of the starting PEGs which are usually defined by their molecular weights rather than the self-repeating unit n, PEGs are normally characterized with a weight average molecular weight, rather than their self-repeating units represented by n. The starting PEG compounds with different molecular weights are readily synthesized using methods known in the art or they are commercially available.

The Y-shape PEG derivatives of the present invention can be synthesized and prepared by general methods in this field. The different compounds claimed in the invention are synthesized and prepared by known methods, which can be found in the technological literatures and patents in this field.

For Pa and Pb being mPEGs, $X_1$ and $X_2$ being a simple branched alkyl, and F being a hydroxyl group, the possible formula is below:

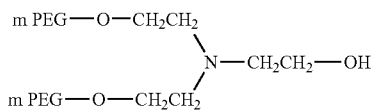

This compound can be prepared by using a standard polymerization initiator, to promote the polymerization of ethylene oxide or ethylene glycol. A standard method of preparation is shown below:

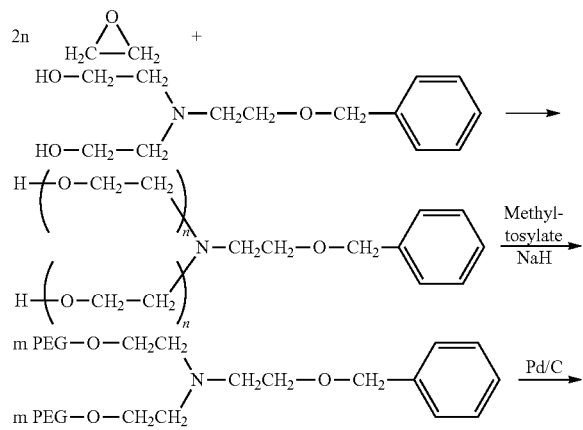

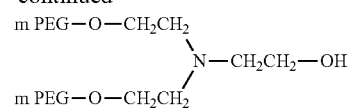

For $P_a$ and $P_b$ being methoxy polyethylene glycols (mPEGs), $X_1$ and $X_2$ being different, the possible formula is below:

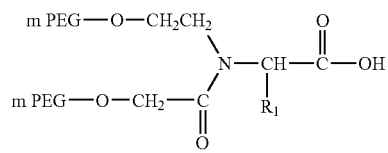

This compound can be obtained from stepwise reactions of a PEG with a compound containing an amino group. The selected compound containing an amino group can be an amino acid, an amino ketone or another molecule having an amino group. The standard preparation route is illustrated below. However, there are other standard methods useful for preparing this derivative that are known in this field.

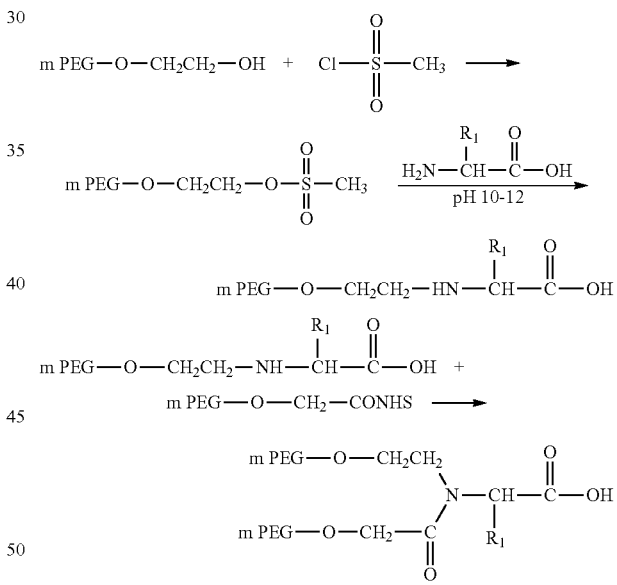

When the hydrophilic polymer derivatives of present invention are used, the F terminal group plays a key role. Derivatives with different terminal groups have different uses. The introduction of these functional groups determines the applicable fields and structures of these derivatives. In respect of the desired use, the following methods can be used to modify the terminal functional group:

1. Amination

Because of greater reactivity of amino groups over hydroxyl groups, the aminated PEG derivatives are important in reacting with a molecule having a carboxylic acid group to yield a conjugate.

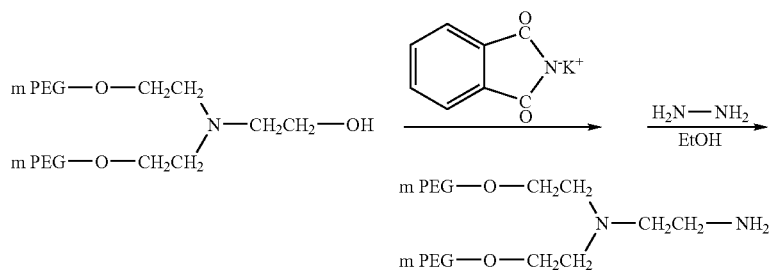

2. Carboxylation

Carboxylation helps to improve PEG's reactivity and makes it capable of conjugating to molecules having amino or hydroxyl groups.

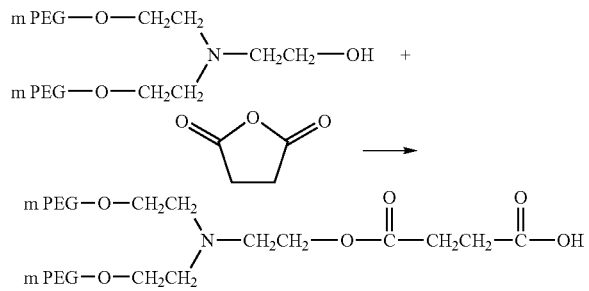

If an amino acid is used as a starting material, the terminal group of the resulting Y-shaped PEG will have a carboxylic group. Especially, if multiple carboxylic acid containing amino acids or polymers are used, the terminal groups will have several carboxylic acid groups. This kind of structure is useful to increase the load of small natural drug molecule and achieve a slow-release effect by stepwise degradation.

3. Other Modification Methods

Other modification, for example, by acid chloride, hydrazine, maleimide, pyridine disulfide and the like can be appropriately adopted as well to obtain corresponding derivatives. Other preparation methods in this field will be apparent to those skilled in this are.

Many components of natural drugs have active functional groups such as amino, carboxyl and hydroxyl groups, which bind with monosaccharides, polysaccharides, nucleosides, polynucleosides, phosphoryl and the like in vivo, to form active pharmacological structures.

Similarly, the PEG derivatives with the modified terminal functional group can conjugate to the drug molecules in the same way to take the place of a bio-organic molecule and overcome the shortcomings of short physiological half-lives and low therapeutic effect. The following model is a general ester synthesis reaction.

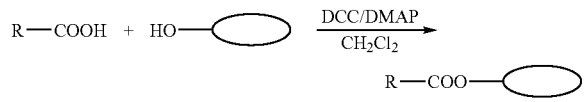

An ester group can be eliminated by biodegradation in vivo to release the active ingredient. An amide group is relatively stable in vivo.

The Y-shape hydrophilic polymer derivatives of the present invention can form conjugates with drug molecules through proper functional groups. These functional groups can link the free amino, hydroxyl or thiol group of proteins, polypeptides and other natural drugs with the polymer derivatives. For proteins and peptides with high molecular weight, one molecule can link with one or more PEG derivatives to improve the physiological effects of the drug molecules in vivo. For the active components of a natural drug with low molecular weight, one PEG derivative can be linked to one or more drug molecules through proper functional groups to ensure a proper drug concentration and the function of sustained release.

The applications described above offer some possible reference models for medical application of the PEG derivatives. The choice of proper derivatives for real applications can be confirmed by using animal pharmacology, toxicology, clinical study and other such approaches.

Preferably, the drug molecules included in the conjugates of the present invention are the active ingredients separated from nature plants, such as paclitaxel, camptothecin, cinobufagin, clycyrrhetinic acid and scopoletin. Preferably, the drugs are the ingredients of natural medicines used in the treatment of tumors, such as paclitaxel, camptothecin, and derivatives thereof. Prefered drugs also include interferons, such as α- and β-interferon.

The conjugates of the present invention can be administered in the form of pure compounds or suitable pharmaceutical compositions, via any acceptable routes or being included in a reagent for similar use. Thus, the conjugates can be administered via oral, nasal, parenteral, topical, transdermal, rectal or injection routes in the form of solid, semisolid, lyophilized powder or liquid, for example, tablets, suppositories, pills, soft and hard gelatin capsules, powder, solution, suspension and aerosols. Preferably the unit dosage form is suitable for a precise-dosage and easy administration. The composition includes conventional pharmaceutical carriers or excipients and the conjugate(s) of the present invention as the active ingredient(s). Furthermore, it also can include other agents, carriers and excipients.

Generally speaking, depending on the method of administration, the pharmaceutically acceptable compositions will include about 1-99 wt. % of the conjugate of the present invention, and 99-1 wt. % of suitable pharmaceutical excipient. Preferably they include 5-75 wt. % of the conjugate and the rest is any suitable pharmaceutical excipient.

The preferable way of administration is injection with a general daily dosage scheme, which can be adjusted based on the severity of the disease to be treated. The conjugates of the present invention or their pharmaceutically acceptable salts may be formulated in the dosage for injection by, for example, dissolving 0.5-50% of the active components in a liquid pharmaceutical carrier, such as water, saline, aqueous glucose, glycerol, ethanol and the like to form a solution of suspension.

The compositions which can be administered as liquid such as solutions and suspensions can be prepared by dissolving and dispersing the conjugate of the present invention (about 0.5-20%) and optionally a the pharmaceutical excipient into a carrier. Example of carriers includes water, saline, aqueous glucose, glycerol, ethanol and the like.

If needed, the pharmaceutical composition of the present invention can further include an adjuvant in a small amount, such as wetting agent, emulsifier, pH buffer, antioxidant and the like. For example, citric acid, sorbitan monolaurate, triethanolamine oleate, butylated hydroxytoluene and the like can be added.

The practical preparation methods of such dosage forms are known or obvious to the skilled in the art. For example, see Ramington's Pharmaceutical Sciences, 18$^{th}$ edition, (Mack Publishing Company, Easton, Pa., 1990). In any case, according to the techniques of the present invention, the composition applied will include an effective amount of the conjugate of the present invention for the treatment of corresponding disease.

EXAMPLES

The polymer derivatives and the conjugates of the present invention and their preparation methods will be further described by the following examples. These examples do not intend to limit the scope of the invention by any means. The scope of the present invention can be determined by the claims.

Example 1

Synthesis of Y-Shape Branched Polyethylene Glycol Derivatives (1)

The synthesis is shown in FIG. 1. At 0° C., 10 ml of dry ethylene oxide was added to a heavy-duty flask, which included 200 mg of N,N-di-2-hydroxylethyl-2-benzyloxyethyl amine and 50 mg of dry NaH. The reaction mixture was stirred with the temperature being slowly increased. After 28 hours, the viscous liquid was quenched with water and the polymer was extracted with dichloromethane. The organic phase was dried with anhydrous sodium sulfate, and the solvent was removed under vacuum. Yield: 8.2 g (81%), Mp: 56-58° C.

5 g of $(PEG)_2$-N—$CH_2CH_2$O-Bz (molecular weight is 10000, obtained from above step) was dissolved in 50 ml toluene. 0.1 g of sodium hydride and 0.5 g of benzene sulfonic acid methyl ester were added to the solution. The reaction mixture was heated at 80° C. for 24 hours. Then the solution was quenched with 2 ml of isopropyl alcohol. The solvent was removed under vacuum and the residue was added to 200 ml of isopropyl alcohol. The precipitate was collected by filtration and dried in vacuum. Yield: 4.6 g (92%), Mp: 57-59° C.

3 g of $(MeO-PEG)_2$-N—$CH_2CH_2$O-Bz (molecular weight is 10000, obtained from above step) was dissolved in 30 ml of anhydrous 1,4-dioxane. Then, 0.1 g of Pd/C was added to the solution mixture as catalyst and $H_2$ gas (40 psi) was introduced into the reactor. The solution was vigorously stirred at room temperature overnight. The catalyst was removed by filtration and was washed with fresh dichloromethane. The solvent was removed by rotary evaporation and the residue was added into ethyl ether. The precipitate was collected by filtration and dried in vacuum. Yield: 2.4 g (80%). NMR (DMSO): 3.5 (br m, H in PEG), 3.24 (s, 6H), 2.63 (t, 6H).

Example 2

Synthesis of Y-Shape Branched Polyethylene Glycol Succinimidyl Carbonate (2)

Figure 2:
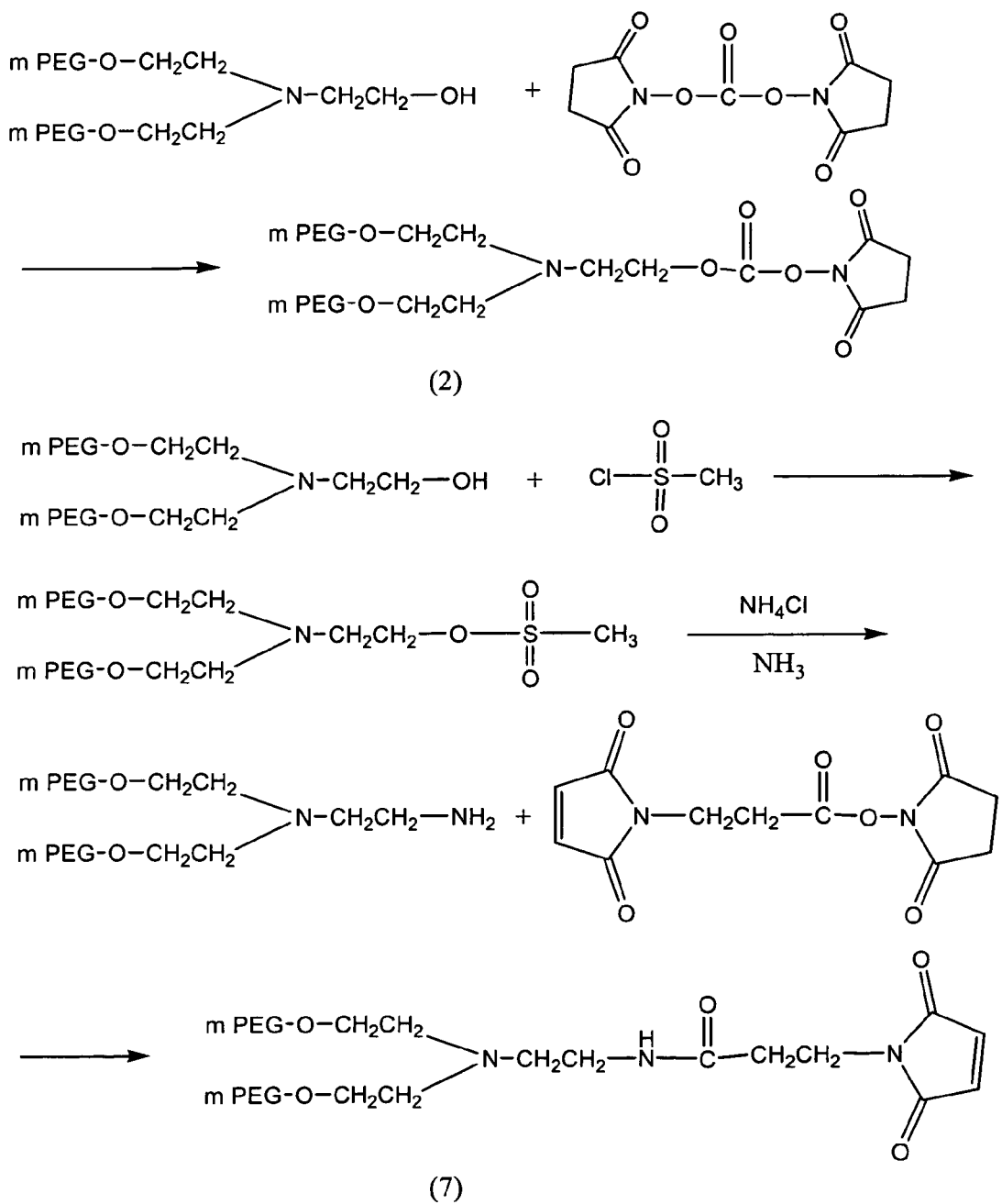
FIG. 2 shows the synthesis of Y-shape branched polyethylene glycol derivatives (2) and (7).

The synthesis is shown in FIG. 2. 1 g of Y-shape branched PEG derivative of Mw 10000 (($MeO-PEG)_2$-N—$CH_2CH_2$OH, from example 1) and 0.1 g of di-succinimidyl carbonate were dissolved in 20 ml of acetonitrile. 0.1 ml of pyridine was added to the solution. The reaction mixture was stirred under the protection of nitrogen overnight. The solvent was removed by rotary evaporation and the residue was dried under vacuum. The solid residue was added to 10 ml of dry dichloromethane. The undissolved solid was filtered. The organic phase was washed with sodium acetate buffer (0.1 M, pH 5.5), dried with anhydrous sodium sulfate, concentrated by rotary evaporation, and precipitated in ethyl ether. The product was dried in vacuum. Yield: 0.9 g (90%). NMR (DMSO): 3.5 (br m, H in PEG), 3.24 (s, 6H), 4.45(t, 2H), 2.82 (s, 4H).

Example 3

Synthesis of mPEG-Glycine (3)

5 g mPEG of molecular weight 5000 was dissolved in 50 ml toluene, azeotropically distilled for 2 hours under the protection of nitrogen, with 10 ml solution being distilled off, and then cooled to room temperature. 3 ml of dry dichloromethane and 0.08 ml dry triethylamine were added to the reaction. The mixture was cooled in an ice-water bath and 0.12 ml of dry methanesulfonyl chloride was added dropwise. The mixture was stirred at room temperature under the protection of nitrogen overnight. The reaction was quenched by adding 2 ml of absolute ethanol. Part of the solvent was removed by rotary evaporation, the precipitate was collected by filtration, and then 150 ml ethyl ether was added. The precipitate was collected by filtration and dried in vacuum. Yield: 4.8 g (96%). NMR(DMSO): 3.5 (br m, H in PEG), 3.24 (s, 3H), 4.32 (t, 2H).

2 g of glycine hydrochloride was dissolved in 20 ml of deionized water. 1 g of NaOH was added to the glycine solution to adjust the pH to 10.5. Then 2 g of mPEG mesylate ester of molecular weight 5000 (obtained from above step) was added to the solution. The solution was incubated at 37° C. for 72 hours, and then neutralized by hydrochloride solution to pH about 7. The polymer was extracted with dichloromethane. The organic phase was dried with anhydrous sodium sulfate and the solvent was removed under vacuum. Yield: 1.7 g (85%), Mp: 55-57° C. NMR (DMSO): 3.5 (br m, H in PEG), 3.24 (s, 3H), 2.95 (t, 2H), 3.11 (s, 2H).

Example 4

Synthesis of mPEG-Alanine (4)

5 g mPEG of molecular weight 5000 was dissolved in 50 ml of toluene, azeotropically distilled for 2 hours under the protection of nitrogen with 10 ml solvent being distilled off, and then cooled to room temperature. 3 ml of dry dichloromethane and 0.08 ml of dry triethylamine were added to the reaction. The mixture was cooled in an ice-water bath and 0.12 ml dry methanesulfonyl chloride was added dropwise.

The mixture was stirred at room temperature under the protection of nitrogen overnight. The reaction was quenched by adding 2 ml of absolute ethanol. The solvent was removed by rotary evaporation, the precipitate was collected by filtration, and then 150 ml ethyl ether was added. The precipitate was collected by filtration and dried in vacuum. Yield: 4.5 g (90%). NMR (DMSO): 3.5 (br m, H in PEG), 3.24 (s, 3H), 4.32 (t, 2H).

2 g of alanine hydrochloride was dissolved in 20 ml of deionized water. 1 g of NaOH was added to the alanine solution to adjust the pH to 10.5. Then 2 g of mPEG mesylate of molecular weight 5000 was added to the solution. The solution was incubated at 37° C. for 72 hours, and then neutralized with hydrochloride solution to pH about 7. The polymer was extracted with dichloromethane. The organic phase was dried with anhydrous sodium sulfate, and the solvent was removed under vacuum. Yield: 1.9 g (94%), Mp: 55-57° C. NMR (DMSO): 3.5 (br m, H in PEG), 3.24 (s, 3H), 2.94 (m, 1H), 1.24 (d, 3H).

Example 5

Synthesis of Y-Shape Branched PEG Derivatives (5) Reactive to an Amino Group

Figure 3:
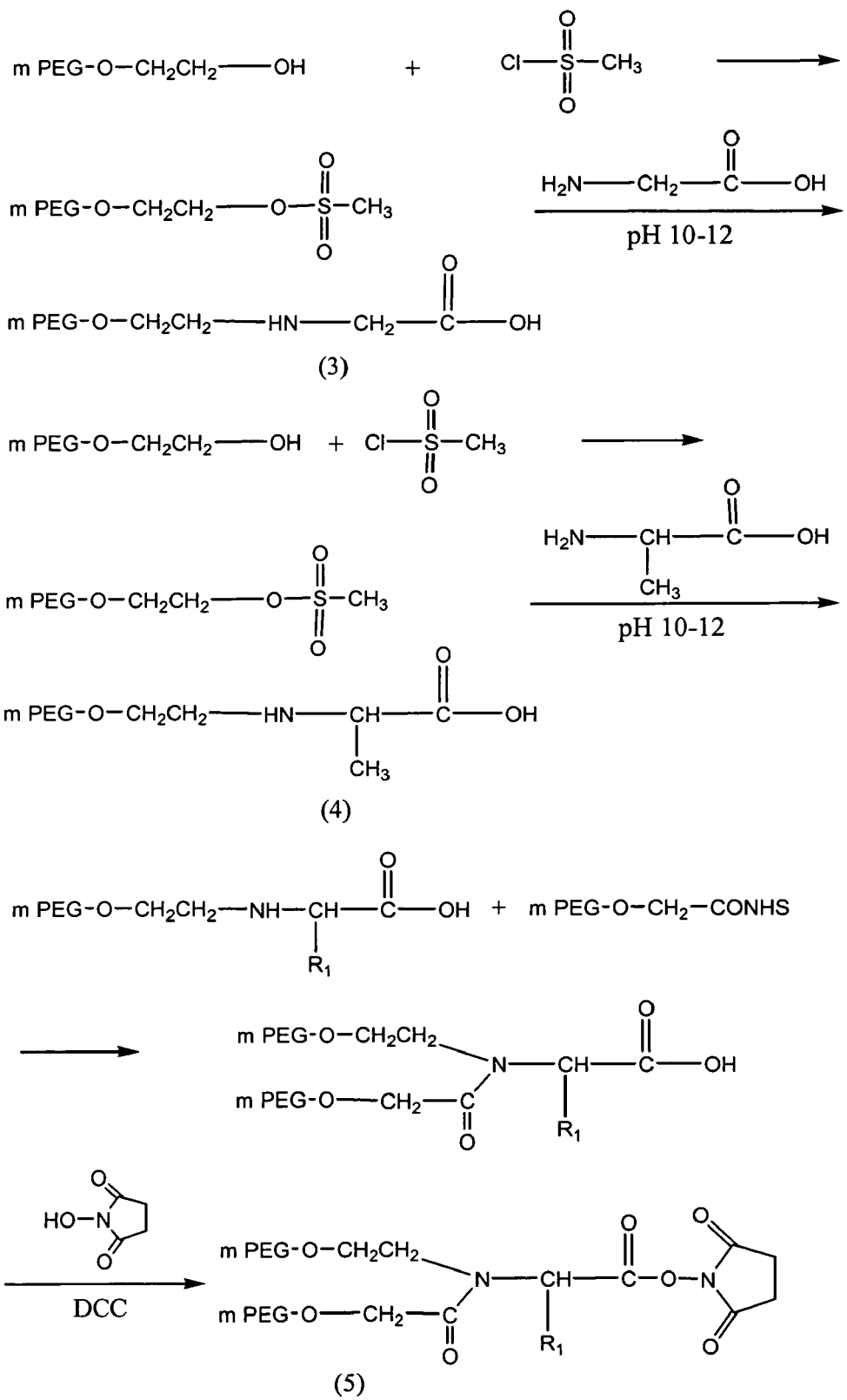
FIG. 3 shows the synthesis of Y-shape branched polyethylene glycol derivatives (5).

The synthesis is shown in FIG. 3. 1 g of mPEG-glycine (3) or mPEG-alanine (4) of molecular weight 5000 (from example 3 or 4) was dissolved in 20 ml of dichloromethane. 1 g of mPEG carboxyethyl NHS ester (mPEG-O—$CH_2$—CO—NHS, molecular weight 5000) and 0.1 ml of triethylamine were added to the solution. The solution was stirred overnight. The solvent was removed under vacuum and the residue was added to ethyl ether. The precipitate was collected by filtration and dried under vacuum. The product (Y-shape branched PEG acid) was further purified by ion exchange chromatography. Yield: 0.98 g (50%).

0.5 g of Y-shape branched MPEG acid was dissolved in 10 ml dichloromethane. 7 mg of N-hydroxylsuccinimide (NHS) and 13 mg of dicyclohexylcarbodiimide (DCC) was added to the solution. The solution was stirred at room temperature for 6 hours. The solvent was removed under vacuum. The residue was added to 20 ml of isopropyl alcohol (IPA). The product was collected by filtration and dried under vacuum. Yield: 0.48 g (96%), NMR (DMSO): 3.5 (br m, H in PEG), 3.24, (s, 6H), 2.81 (s, 4H), 4.15 (s, 2H), 4.07 (t, 2H), 4.48 (t, 2H).

Example 6

Synthesis of Y-Shape Branched PEG Derivatives (6) Reactive Toward Amine Group

Figure 4:
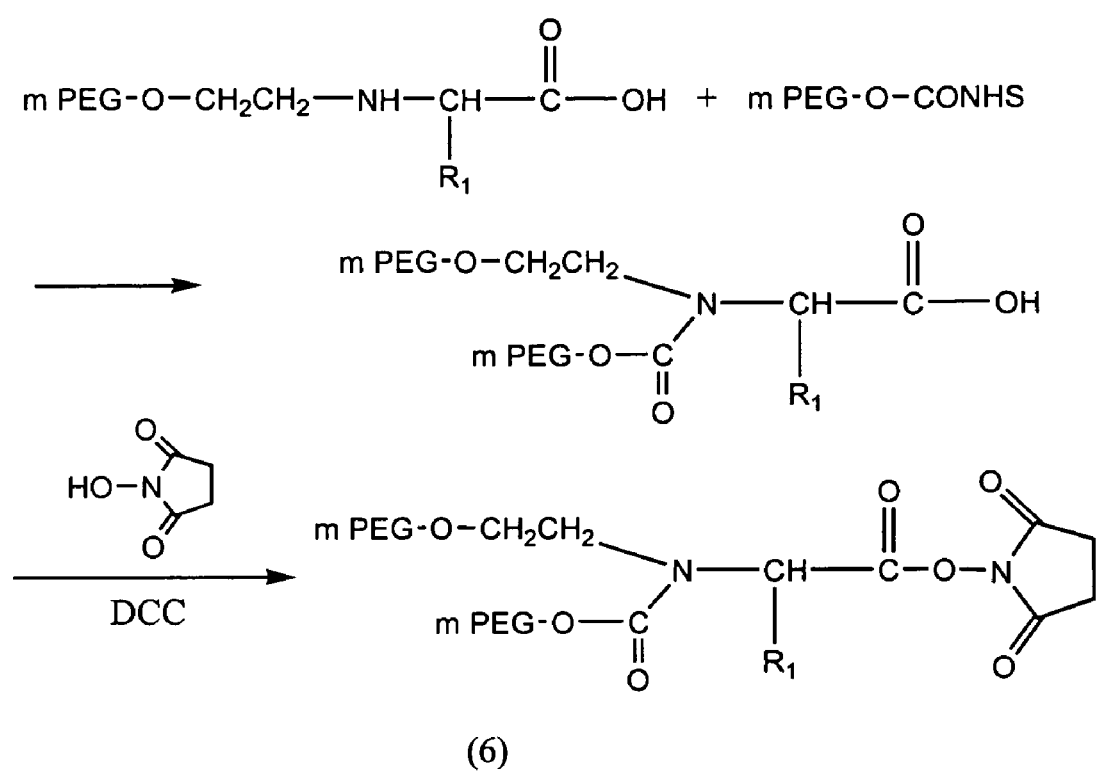
FIG. 4 shows the synthesis of Y-shape branched polyethylene glycol derivatives (6).

The synthesis is shown in FIG. 4. 1 g of mPEG-glycine (3) or mPEG-alanine (4) of molecular weight 5000 (from example 3 or 4) was dissolved in 20 ml of dichloromethane. 1 g of mPEG NHS carbonate (mPEGO-CO—NHS) of Mw 5000 Dalton and 0.1 ml of triethylamine were added to the solution. The solution was stirred overnight. The solvent was removed under vacuum and the residue was added to ethyl ether. The precipitate was collected by filtration and dried under vacuum. The product (Y-shape branched PEG acid) was further purified by ion exchange chromatography. Yield 0.98 g (50%).

0.5 g of Y-shape branched mPEG acid was dissolved in 10 ml dichloromethane. 7 mg of N-hydroxylsuccinimide (NHS) and 13 mg of dicyclohexylcarbodiimide were added to the solution. The solution was stirred at room temperature for 6 hours. The solvent was removed under vacuum. The residue was added to 20 ml of isopropyl alcohol. The precipitate was collected by filtration and dried under vacuum. Yield 0.48 g (96%). NMR (DMSO): 3.5 (br m, H in PEG), 3.24 (s, 6H), 2.81 (s, 4H), 4.15 (s, 2H), 4.07 (t, 2H).

Example 7

Synthesis of Y-Shape Branched PEG Derivatives (7) Reactive Toward Thiol Group

The synthesis is shown in FIG. 2. 1 g of Y-shape branched PEG ((MeO-PEG)$_2$-$NCH_2CH_2OH$) of molecular weight 10000 (obtained in Example 2) was dissolved in toluene, azeotropically distilled for 2 hours under protection of nitrogen, and then cooled to room temperature. 3 ml of dry dichloromethane and 0.08 ml dry triethylamine were added to the solution. The mixture was cooled in an ice-water bath and dry methanesulfonyl chloride was added dropwise. The mixture was stirred at room temperature under dry nitrogen overnight. The reaction was quenched by adding 3 ml of absolute ethanol. The solvent was removed by rotary evaporation, the precipitate was removed by filtration, and then 150 ml of ethyl ether was added. The precipitate was collected by filtration and dried in vacuum. Yield: 0.8 g (80%).

1 g of Y-shape branched PEG mesylate ((MeO-PEG)$_2$-N—$CH_2CH_2O$ Ms) of molecular weight 10000 was dissolved in 30 ml of aqueous ammonia solution with 5% ammonium chloride. The solution was stirred over 72 hours at room temperature. The solution was extracted with dichloromethane three times. The combined organic phase was dried with anhydrous sodium sulfate. The solvent was removed under vacuum. The residue was added to 50 ml isopropyl alcohol. The precipitate was collected and dried under vacuum. Yield: 0.7 g (70%).

0.5 g of Y-shape branched PEG amine ((MeO-PEG)$_2$-N—$CH_2CH_2NH_2$) was dissolved in acetonitrile. 20 mg of NHS-3-maleimidopropionate was added to the solution. The solution was stirred overnight at room temperature. The solvent was removed under vacuum. The residue was added to 30 ml isopropyl alcohol. The precipitated was collected and dried under vacuum. Yield: 0.42 g (84%). NMR (DMSO): 3.5 (br m, H in PEG), 3.24 (s, 6H), 3.05 (t, 2H), 2.56 (t, 2H), 6.71 (s, 2H in maleimide).

Example 8

Conjugate of Y-Shape Branched PEG-NHS Derivatives with α-Interferon (8)

Figure 7:
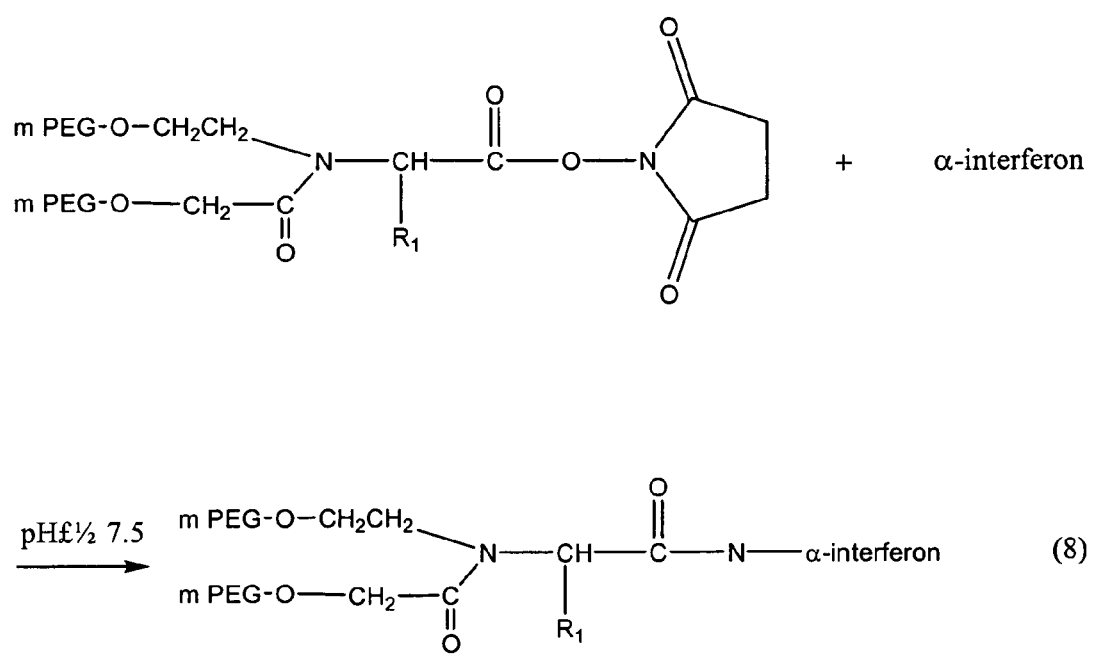
FIG. 7 shows the synthesis of conjugates of Y-shape branched polyethylene glycol derivatives and proteins.

The synthesis is shown in FIG. 7. 75 mg Y-shape branched polyethylene glycol succinimidyl ester (from example 2, 5 or 6) was dissolved in 5 ml of buffered α-interferon solution with interferon concentration 5 mg/ml (pH 7.4). In the reaction solution PEG and α-interferon were at ratio of 3:1. The solution was gently shaken for 1 hour at 4° C. and then 5 hours at room temperature. The solution was diluted to a final interferon concentration of 0.5 mg/ml and purified by HPLC with gel column. The mono-substituted Y-shape branched PEG conjugate of α-interferon was collected. SDS-PAGE showed the product contained no free α-interferon.

SDS-PAGE Analysis: Reaction mixture and the purified PEG-IFN was subjected to sodium dodecyl (lauryl) sulfate/polyacrylamide (8-16%) gel electrophoresis and stained for protein using Coomassie blue dye. PEG moieties in the PEG2-IFN conjugates were specifically stained using Titrisol iodine solution (EM Science, Gibbstown, N.J.). The SDS-PAGE gel was rinsed with distilled water and placed in 5% barium chloride solution. After 10 min, the above gel was washed with distilled water and placed in 0.1 N Titrisol iodine solution for another 10 min. Titrisol was washed off with distilled water. The PEG stained (orange brown bands) SDS-PAGE gel containing Y-PEG-IFN samples was stored in distilled water in a heat-sealed Kapak/Scotchpak bag.

Example 9

Conjugate of Y-Shape Branched PEG-NHS Derivatives with β-Interferon

Y-shape branched polyethylene glycol succinimidyl ester (Example 5 or 6) was dissolved in 5 ml of buffered β-interferon solution with interferon concentration of 1 mg/ml (pH 7.4). In the reaction solution, PEG and β-interferon were at ratio of 3:1. The solution was gently shaken for 7 hours. The solution was purified by HPLC with gel column. The monosubstituted Y-shape branched PEG conjugate of β-interferon was collected. SDS-PAGE and CE showed the product contains no free β-interferon.

Example 10

Conjugate of Y-Shape Branched PEG Derivatives with Paclitaxel (10)

Figure 5:
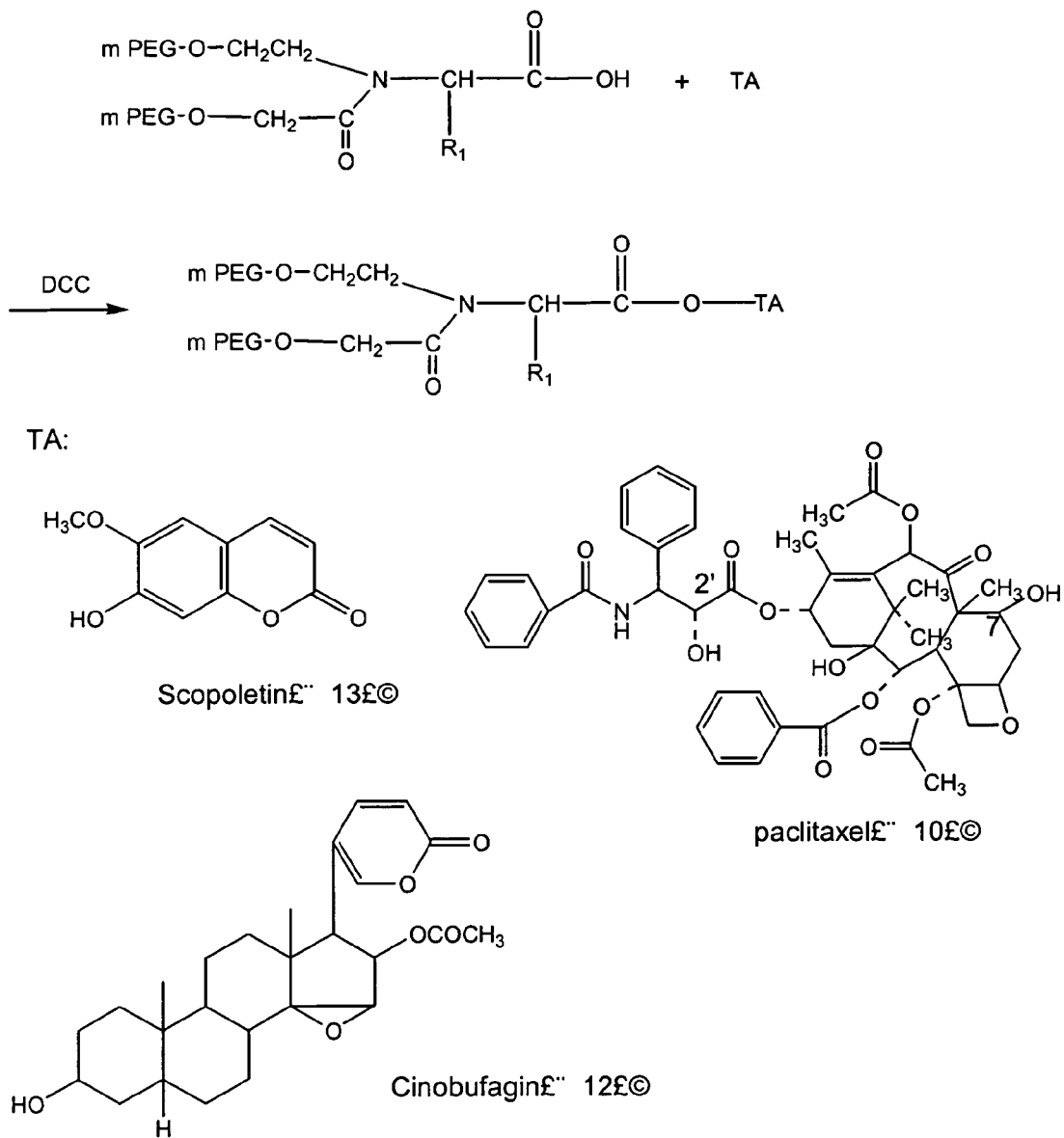
FIG. 5 shows the synthesis of conjugates of Y-shape branched polyethylene glycol derivatives (1) and drugs (through ester bonds).

The synthesis is shown in FIG. 5. 1 g of Y-shape branched PEG carboxylic acid (from Example 5 or 6) was dissolved in 10 ml dichloromethane. 90 mg of paclitaxel, 8 mg of dimethylamino pyridine and 25 mg of dicyclohexylcarbodiimide were added to the solution. The solution was stirred at room temperature for 6 hours. The solvent was removed under vacuum. The residue was added to 20 ml of isopropyl alcohol. The precipitate was collected by filtration, washed with ether and dried under vacuum. Yield: 0.8 g (80%), Mp: 55-57° C.

Example 11

Conjugate of Y-Shape Branched PEG Derivatives with Camptothecin (11)

Figure 6:
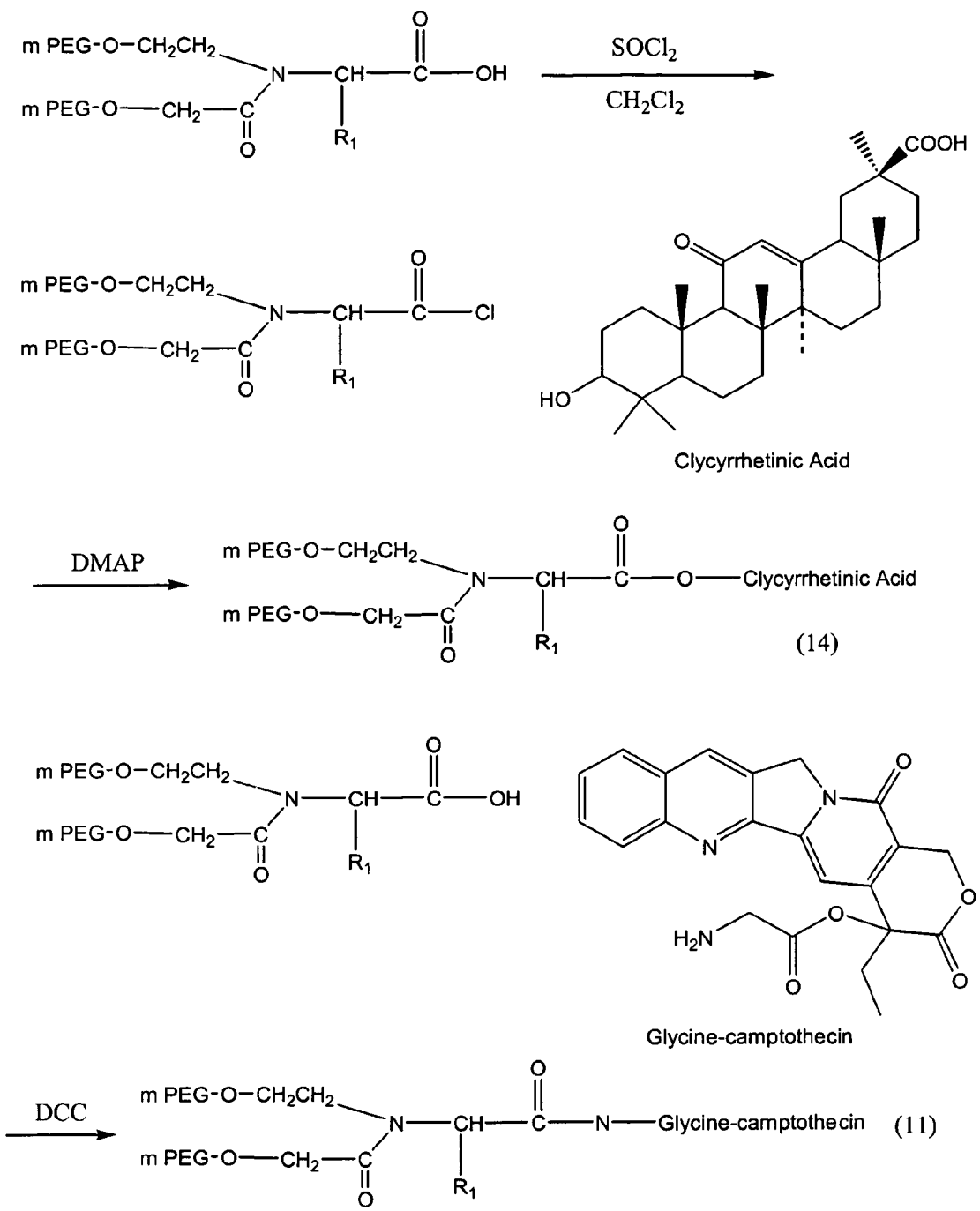
FIG. 6 shows the synthesis of conjugates of Y-shape branched polyethylene glycol derivatives and drugs (through other bonds).

The synthesis is shown in FIG. 6. 1 g of Y-shape branched PEG carboxylic acid (Example 5 or 6) was dissolved in 10 ml dichloromethane. 120 mg of glycine-camptothecin, 50 mg of dimethylamino pyridine and 95 mg of dicyclohexylcarbodiimide were added to the solution. The solution was stirred at room temperature for 6 hours. The solvent was removed under vacuum. The residue was dissolved in 20 ml of 1,4-dioxane. The precipitate was removed by filtration. The solution was concentrated, and the residue was added to 20 ml of ethyl ether. The precipitate was collected by filtration, washed with ethyl ether and dried under vacuum. Yield: 0.8 g (80%), Mp: 56-58° C.

Example 12

Conjugate of Y-Shape Branched PEG Derivatives with Cinobufagin (12)

The synthesis is shown in FIG. 5. 1 g of Y-shape branched PEG carboxylic acid (Example 5 or 6) was dissolved in 10 ml dichloromethane. 60 mg of Cinobufagin, 12 mg 1-Hydroxybenzotriazole, 16 mg of dimethylamino pyridine and 40 mg of dicyclohexyl-carbodiimide were added to the solution. The solution was stirred at room temperature for 6 hours. The solvent was removed under vacuum. The residue was added to 20 ml of isopropyl alcohol. The precipitate was collected by filtration, washed with ether and dried under vacuum. Yield: 0.75 g (75%), Mp: 57-59° C.

Example 13

Conjugate of Y-Shape Branched PEG Derivatives with Scopoletin (13)

The synthesis is shown in FIG. 5. 1 g of Y-shape branched PEG carboxylic acid (Example 5 or 6) was dissolved in 20 ml of dichloromethane. 30 mg of Cinobufagin, 20 mg of 1-Hydroxybenzotriazole, 20 mg of dimethylamino pyridine and 38 mg of dicyclohexyl-carbodiimide were added to the solution. The solution was stirred at room temperature for 12 hours under the protection of nitrogen. The solvent was concentrated under vacuum. The residue was added to 20 ml of 1,4-dioxane. The precipitate was collected by filtration, washed with ether and dried by air exhaust. The solvent was removed under vacuum. The remaining residue was added to 100 ml of isopropyl alcohol. The precipitate was collected by filtration, washed with ether and dried by air exhaust. The precipitates were combined and dried under vacuum. Yield: 0.92 g (92%), Mp: 56-58° C.

Example 14

Conjugate of Y-Shape Branched PEG Derivatives with Clycyrrhetinic Acid (14)

The synthesis is shown in FIG. 6. 1 g of Y-shape branched PEG carboxylic acid (Example 5 or 6) was dissolved in 10 ml of dichloromethane. 0.2 ml of thionyl chloride was added to the solution. The solution was stirred for 2 hours. The solvent and impurities having low boiling point were removed under vacuum. 10 ml of dichloromethane solution having 70 mg clycyrrhetinic acid was added, and dissolved by mixing. Then 60 mg 4-dimethylamino pyridine was added. The reaction mixture was stirred for 12 hours at room temperature under the protection of nitrogen gas. The solvent was concentrated under vacuum. The residue was added into 20 ml of isopropyl alcohol. The precipitate was collected by filtration, washed with ethyl ether, dried by air exhaust, and further dried under vacuum. Yield: 0.6 g (60%). M.p.: 58~60° C.

Example 15

This example is to illustrate the preparation process of a typical pharmaceutical composition administered parenterally. The composition comprises the conjugate of the present invention.

| Component | |
| --- | --- |
| Conjugate prepared in Example 8 | 2 g |
| 0.9% saline | 100 ml |

The conjugate prepared in Example 8 was dissolved in 0.9% saline to obtain 100 ml solution for intravenous injection, which was filtered through 0.2 μm membrane and packed aseptically. The powder for injection was obtained by freeze-drying.

We claim:

1. A Y-shaped branched hydrophilic polymer derivative as set forth by formula I:

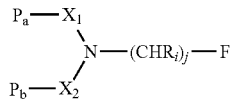

(I)

wherein $P_a$ and $P_b$ are hydrophilic polymers, which are the same or different;

j is an integer from 1 to 12;

$R_i$ is selected from the group consisting of H, a $C_{1-12}$ substituted or unsubstituted alkyl, a substituted aryl, an aralkyl, and a heteroalkyl;

$X_1$ and $X_2$ independently are linking groups, wherein $X_1$ is $(CH_2)_n$, and $X_2$ is $(CH_2)_n CO$, wherein n is an integer of from 1-10; and F is a functional group capable of reacting with an amino group, a hydroxyl group, or a thiol group of a therapeutic agent or a substrate to form a covalent linkage, selected from the group consisting of a hydroxyl group, a carboxyl group, an ester group, carboxylic acid chloride, hydrazide, maleimide and pyridine disulfide.

2. The hydrophilic polymer derivative of claim 1 wherein the hydrophilic polymer is selected from the group consisting of polyethylene glycol, polypropylene glycol, polyvinyl alcohol, polyacrylmorpholine and copolymers thereof.

3. The hydrophilic polymer derivative of claim 2 wherein the hydrophilic polymer is polyethylene glycol.

4. A Y-shaped branched polyethylene glycol (PEG) derivative as set forth by formula III:

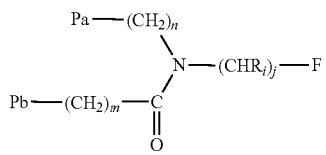

(III)

wherein $P_a$ and $P_b$ are polyethylene glycols, which are the same or different;

n, m and j are independently an integer from 1 to 12;

$R_i$ is selected from the group consisting of H, a $C_{1-12}$ substituted or unsubstituted alkyl, a substituted aryl, an aralkyl, and a heteroalkyl; and F is a functional group capable of reacting with an amino group, a hydroxyl group, or a thiol group of a therapeutic agent or a substrate to form a covalent linkage, selected from the group consisting of a hydroxyl group, a carboxyl group, an ester group, carboxylic acid chloride, hydrazide, maleimide and pyridine disulfide.

5. The derivative of claim 1, wherein $P_a$ and $P_b$ are the same or different polyethylene glycols (PEGs) of formula (V):

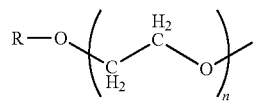

(V)

wherein

R is H, a $C_{1-12}$ alkyl, a cycloalkyl or an aralkyl; and n is an integer, representing the degree of polymerization.

6. The derivative of claim 5, wherein R is selected from the group consisting of H, methyl, ethyl, isopropyl, cyclopropyl, cyclobutyl, cyclohexyl and benzyl.

7. The derivative of claim 5, wherein the molecular weight of PEG is from about 300 to 60000.

8. A method to prepare the PEG derivative of claim 4, comprising:

reacting one methoxyl polyethylene glycol mesylate with an amino acid under basic conditions to produce a reactive product; and reacting the reactive product obtained above with another methoxyl polyethylene glycol derivative.

9. The method of claim 8, wherein the another methoxyl polyethylene glycol derivative is mPEG-carboxyethyl NHS ester.

10. A conjugate formed by reacting the derivative of claim 1 with a drug molecule through the terminal group F.

11. The conjugate of claim 10 wherein the drug is selected from the group consisting of amino acids, proteins, enzymes, nucleosides, saccharides, organic acids, glycosides, flavonoids, anthraquinones, terpenoids, phenylpropanoid phenols, steroids, glycosides of the steroids and alkaloids of the steroids.

12. The conjugate of claim 10 wherein the drug is an active component of a natural medicine.

13. The conjugate of claim 12 wherein the active component is cinobufagin, clycyrrhetinic acid or scopoletin.

14. The conjugate of claim 10 wherein the drug is an anti-tumor agent.

15. The conjugate of claim 14 wherein the anti-tumor agent is selected from the group consisting of paclitaxel, camptothecin, interferon and derivatives thereof.

16. The conjugate of claim 15 wherein the interferon is α-, β- or γ-interferon.

17. A pharmaceutical composition comprising the conjugate according to claim 10 and a pharmaceutically acceptable carrier or excipient.

18. The derivative of claim 4, wherein $P_a$ and $P_b$ are the same or different polyethylene glycols (PEGs) of formula (V):

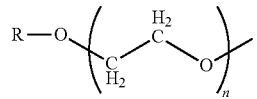

(V)

wherein

R is H, a $C_{1-12}$ alkyl, a cycloalkyl or an aralkyl; and n is an integer, representing the degree of polymerization.

19. The derivative of claim 18, wherein R is selected from the group consisting of H, methyl, ethyl, isopropyl, cyclopropyl, cyclobutyl, cyclohexyl and benzyl.

20. The derivative of claim 19, wherein the molecular weight of PEG is from about 300 to 60000.

21. The method of claim 8, further comprising a step of derivatizing to incorporate the functional group F of claim 4.

22. A conjugate formed by reacting the derivative of claim 4 with drug molecules through the terminal group F.

23. The conjugate of claim 22 wherein the drug is selected from the group consisting of amino acids, proteins, enzymes, nucleosides, saccharides, organic acids, glycosides, flavonoids, anthraquinones, terpenoids, phenylpropanoid phenols, steroids, glycoside of the steroids and alkaloids of the steroids.

24. The conjugate of claim 22 wherein the drug is an active component of a natural medicine.

25. The conjugate of claim 22 wherein the active component is cinobufagin, clycyrrhetinic acid or scopoletin.

26. The conjugate of claim 22 wherein the drug is an anti-tumor agent.

27. The conjugate of claim 26 wherein the anti-tumor agent is selected from the group consisting of paclitaxel, camptothecin, interferon and derivatives thereof.

28. The conjugate of claim 27 wherein the interferon is α-, β- or γ-interferon.

29. A pharmaceutical composition comprising the conjugate according to claim 22 and a pharmaceutically acceptable carrier or excipient.

* * * * *